(12) United States Patent
Takeuchi et al.

(10) Patent No.: US 6,998,615 B2
(45) Date of Patent: Feb. 14, 2006

(54) METHOD FOR EVALUATING PIEZOELECTRIC FIELDS

(75) Inventors: Hideo Takeuchi, Tokyo (JP);
Yoshitsugu Yamamoto, Tokyo (JP);
Takahide Ishikawa, Tokyo (JP)

(73) Assignee: Mitsubishi Denki Kabushiki Kaisha, Tokyo (JP)

( * ) Notice: Subject to any disclaimer, the term of this patent is extended or adjusted under 35 U.S.C. 154(b) by 25 days.

(21) Appl. No.: 10/768,163

(22) Filed: Feb. 2, 2004

(65) Prior Publication Data

US 2004/0155194 A1   Aug. 12, 2004

(30) Foreign Application Priority Data

Feb. 12, 2003   (JP)   ............................. 2003-033306

(51) Int. Cl.
*G01R 29/22* (2006.01)

(52) U.S. Cl. .................................. 250/341.1; 324/727
(58) Field of Classification Search ............ 250/341.1, 250/227.28, 227.29; 324/727; 356/300, 356/369, 445, 624
See application file for complete search history.

(56) References Cited

U.S. PATENT DOCUMENTS

| | | | | |
|---|---|---|---|---|
| 4,589,783 A | * | 5/1986 | Thomas et al. | 374/45 |
| 4,632,549 A | * | 12/1986 | Czabaffy et al. | 356/300 |
| 4,765,742 A | * | 8/1988 | Davinson | 356/624 |
| 5,255,071 A | | 10/1993 | Pollak et al. | |
| 5,982,499 A | * | 11/1999 | Chichester et al. | 356/445 |
| 6,362,881 B1 | * | 3/2002 | Pickering et al. | 356/369 |
| 2003/0229458 A1 | * | 12/2003 | Alfano et al. | 702/40 |

FOREIGN PATENT DOCUMENTS

JP   3-175340   7/1991

OTHER PUBLICATIONS

Shen et al., "Franz-Keldysh Oscillations In Modulation Spectroscopy," *American Institute of Physics, J. Appl. Phys.,* Aug. 15, 1995, pp. 2151-2175, vol. 78(4).

Weisbuch et al., "Quantum Semiconductor Structures: Fundamentals and Applications," *Academic Press, 1991, pp. 18-23.*

Liu et al., "Intersubband Transitions in Quantum Wells: Physics and Device Applications I," *Academic Press, 2000, pp. 4-19, vol. 62.*

* cited by examiner

*Primary Examiner*—David Porta
*Assistant Examiner*—Faye Polyzos
(74) *Attorney, Agent, or Firm*—Leydig, Voit & Mayer, Ltd.

(57) ABSTRACT

In a method of evaluating a piezoelectric field, non-destructive spectrometry of piezoelectric fields is performed in a semiconductor heterojunction using a technique different from PR spectroscopy. In the method, at first, first and second absorption spectra are measured by irradiating the sample with infrared light at first and second angles, respectively. Then, a peak position of an absorption band having incident-angle dependent intensity is specified, based on the first and second absorption spectra. Thus, the piezoelectric field strength is obtained using a relationship between the piezoelectric field and an electron energy level corresponding to the peak position.

6 Claims, 5 Drawing Sheets

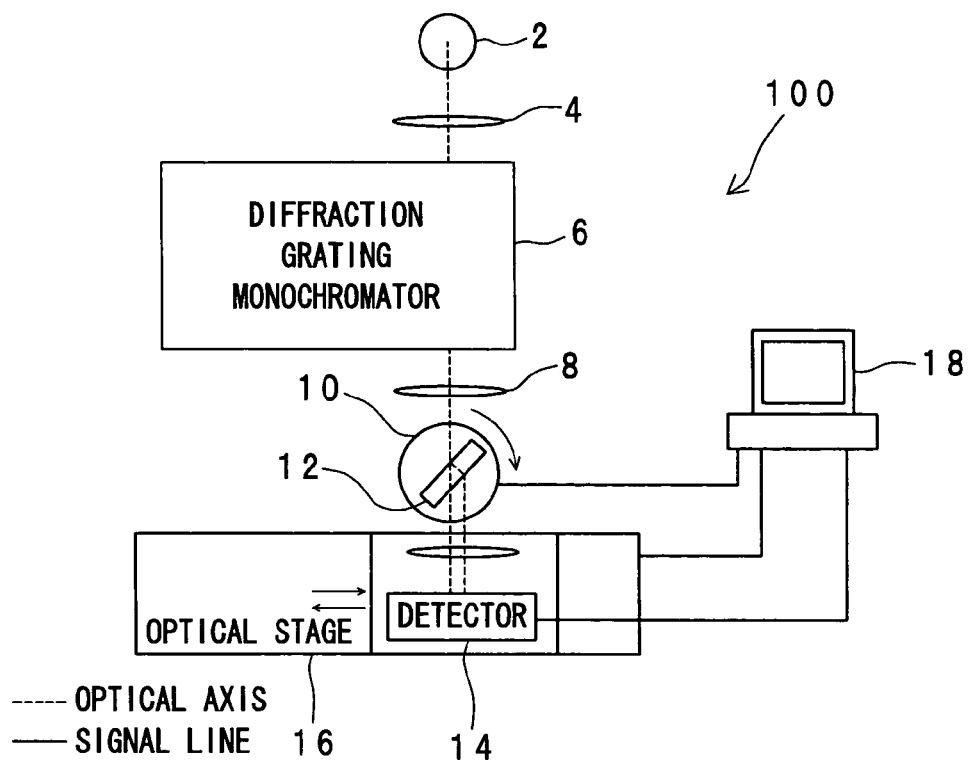
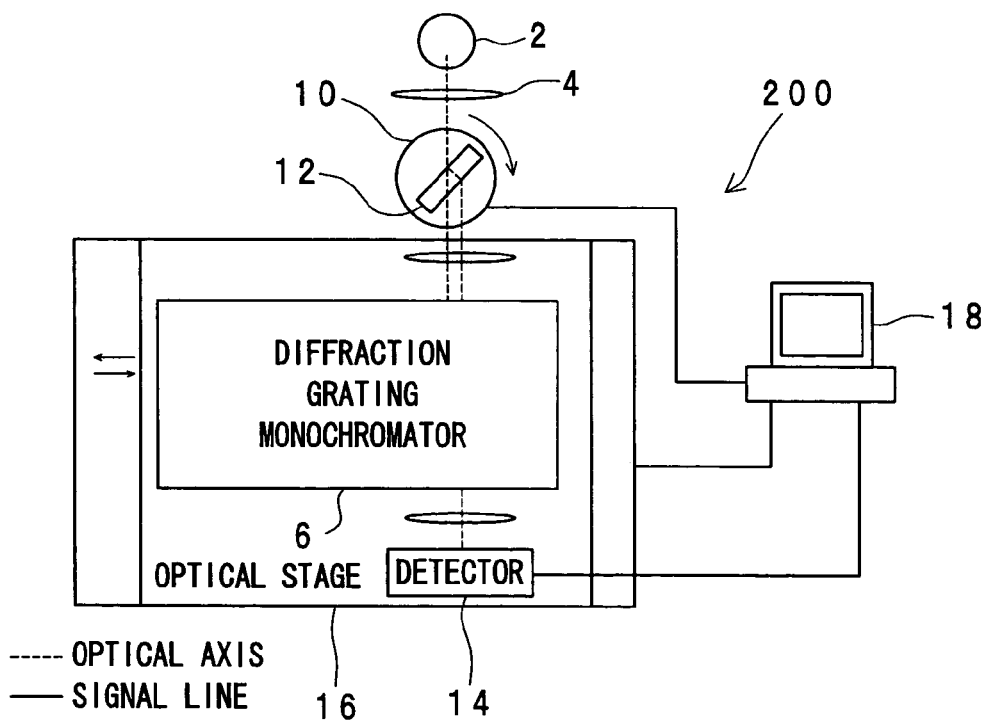

METHOD FOR EVALUATING PIEZOELECTRIC FIELDS

BACKGROUND OF THE INVENTION

1. Field of the Invention

The present invention relates to a spectrometry technique for evaluating a piezoelectric field in an epitaxial layer without destroying the crystal.

2. Description of the Related Arts

The density of two-dimensional electron gas formed at an AlGaN/GaN interface gives the greatest influence to the performance of high electron mobility transistors (referred to as "HEMT" hereinafter) of an AlGaN/GaN type. The density of the two-dimensional electron gas is determined by a sort of internal electric fields called as a piezoelectric field induced by a lattice-mismatch strain peculiar to a semiconductor heterojunction. Therefore, the evaluation of the piezoelectric field is considered to be important upon testing the quality of epitaxial layer structures for the HEMTs.

It has been generally known that photoreflectance (PR) spectroscopy is effective for evaluating the internal electric fields in the crystal such as the above-mentioned piezoelectric field (for example, see Japanese Laid-open Patent publication No. 3-175340). In the PR spectroscopy, the reflectance change $\Delta R/R$, which is caused by the irradiation of the pump light to the sample, is recorded as a function of photon energy with the use of the so-called probe light. In the samples with internal electric fields, the spectra of the reflectance change $\Delta R/R$ exhibits oscillatory patterns called as Franz-Keldysh oscillations (FKOs). The period of the oscillatory patterns is determined by the strength of the internal electric fields. Accordingly, the internal electric field strength can be evaluated through the analysis of the period of the Franz-Keldysh oscillations.

However, it is extremely difficult to measure and evaluate the piezoelectric field at the AlGaN/GaN interface by using the PR spectroscopy. Specifically, the analysis of PR spectra has the complicated procedure for extracting the piezoelectric field from a PR signal. The reason is as follows. In case where the PR spectroscopy is applied to the AlGaN/GaN epitaxial layer structures, the detected reflectance change $\Delta R/R$ is sum of the signals originating from the layers that produces carriers owing to the pump-light irradiation. Therefore, it includes information about the internal electric fields of various layers.

In order to solve the above-mentioned problem, pre processes, where a portion other than the vicinity of the target AlGaN/GaN interface is etched off, seem to be useful ways to perform the PR measurement. However, the etching process gives rise to the problem that the sample should be destroyed. Moreover, in the etching process, surface electric field components, which are caused by a defect introduced to the sample by the etching, may emerge. Signals associated with the surface electric fields overlap with the component originating from the piezoelectric field, thereby resulting in a more complicated signal analysis.

SUMMARY OF THE INVENTION

The purpose of the present invention is to provide a method for analyzing and evaluating a piezoelectric field using a non-destructive spectrometry of piezoelectric fields at a semiconductor heterojunction, which is different from PR measurements.

A method of evaluating a piezoelectric field according to the present invention includes the first to fourth steps. In the first step, an absorption spectrum of a sample is measured with the irradiation of infrared light to the sample at a given angle. In the second step, another absorption spectrum of the sample is measured with the infrared light irradiation to the sample at an angle different from the angle applied to the first step. In the third step, a peak position of an absorption band, which exhibits incident-angle dependent intensity, is specified based on the comparison of the first and the second absorption spectra. In the fourth step, piezoelectric field strength is estimated on the basis of an equation representing a relationship between the piezoelectric field and an electron energy level corresponding to the peak position.

Alternatively, in the second step, the second absorption spectrum of the sample may be measured with the infrared light irradiation to the sample placed on a turntable, which rotates within the range between the predetermined angles in order to modulate the angle of incidence.

In the method, the sample is illuminated by infrared light while changing the angle, whereby the peak position of the absorption band with the incident-angle dependent intensity is specified. Then, the piezoelectric field strength is obtained on the basis of the equation of the energy level representing the above-mentioned relationship. This allows to quantitatively evaluate the piezoelectric field induced by the lattice-mismatch strain peculiar to the semiconductor heterojunction of the sample without destroying or processing the sample. Further, the estimation of the piezoelectric field can lead to the evaluation of the performance of the semiconductor device fabricated from the epitaxial layer structure. Thus, the above-mentioned object can be attained.

BRIEF DESCRIPTION OF THE DRAWINGS

Various characteristics and advantages of the present invention will become clear from the following description taken in conjunction with the preferred embodiments with reference to the accompanying drawings throughout which like parts are designated by like reference numerals, in which:

FIG. 1 is a block diagram showing a configuration of an infrared absorption spectrometer according an embodiment 1;

FIG. 2 is a view showing a configuration of an infrared absorption spectrometer according to another example using a diffraction grating monochromator;

DETAILED DESCRIPTION OF THE PREFERRED EMBODIMENTS

Figure 3:
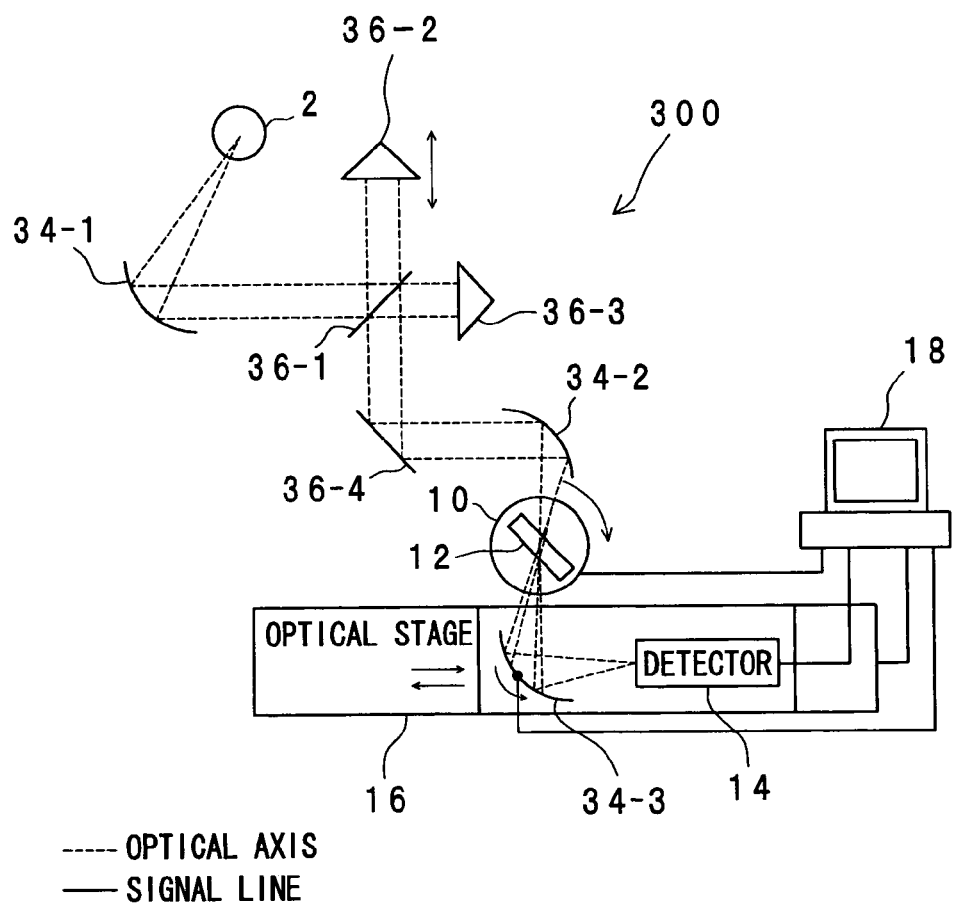
FIG. 3 is a view showing a configuration of an infrared absorption spectrometer utilizing a Fourier transform spectrometer instead of the diffraction grating monochromator.

Embodiments of the invention will be explained with reference to the attached drawings. Like parts having like configurations and functions are given by same numerals in the drawings.

(First Embodiment)

The first embodiment of the present invention relates to a non-destructive evaluation method of a piezoelectric field at an interface of a semiconductor heterojunction using infrared absorption spectroscopy, and a configuration of a device useful for executing this method. The way how to evaluate the piezoelectric field will be explained. The piezoelectric field is induced by a lattice-mismatch strain peculiar to the semiconductor heterojunction. This piezoelectric field determines the density of two-dimensional electron gas formed at the AlGaN/GaN interface. The two-dimensional electron gas gives the greatest influence to the performance of a high electron mobility transistor (HEMT) of an AlGaN/GaN type. Accordingly, the piezoelectric field should be quantitatively evaluated upon testing a quality of the epitaxial layer structures for the HEMTs.

At first, the configuration of a device is explained, and then, the evaluating method with the use of this device is explained.

FIG. 1 shows the configuration of an infrared absorption spectrometer 100 according to the first embodiment. The infrared absorption spectrometer 100 is configured to use a diffraction grating spectrometer (diffraction grating monochromator), wherein a sample is illuminated by infrared light to measure an infrared absorption spectrum. Infrared absorption bands caused only by the transition of the two-dimensional electron gas, which is formed at the AlGaN/GaN interface, are obtained from the measured infrared absorption spectrum, thereby quantitatively evaluating the piezoelectric field.

The infrared light absorbed by being "caused only by the two-dimensional electron gas" can be measured as follows. The infrared light has a characteristic such that the absorption of the infrared light is allowed only in the case where the polarization vector of the infrared light is parallel to the growth direction of the epitaxial layer structures (hereinafter referred to as "z-axis"). Therefore, a comparison is made between the two absorption spectra: one is obtained in case where the infrared light illuminates at oblique incidence, and the other is done in case where the infrared light is incident vertical to the z-axis. Because it can easily be judged which absorption band has the incident-angle dependent intensity, it can be determined based on the comparison result whether the observed absorption band is brought about the two-dimensional electron gas or not. In the infrared absorption spectrometer 100, a table on which the sample is placed, is rotated to change the direction of the infrared light incident to the sample, to thereby judge the presence of incident angle dependence.

The configuration of the infrared absorption spectrometer 100 will be specifically explained hereinafter. The infrared absorption spectrometer 100 has a light source 2, a lens 4, a diffraction grating monochromator 6, another lens 8, a turntable (rotating table) 10, a detector 14, an optical stage 16 and a unit 18.

The lens 4 collects the light emitted from the light source 2. The diffraction grating monochromator 6 equipped with a diffraction grating having a predetermined grating interval receives the light and spectrum-resolves the light (infrared light) having a predetermined wavelength. The wavelength range of the spectrum-resolved infrared light is, for example, from approximately several $\mu$m to several ten $\mu$m. The above-mentioned range is obtained as follows. The piezoelectric field strength is expected to be 0.1 to 1.0 MV/cm. This value leads to the transition energy with the use of the equation described later. The lens 8 focuses the infrared light onto the sample.

On the turntable 10, a sample 12 is placed. The turntable 10 has a rotating mechanism. Rotating the turntable 10 can facilitate the measurement of the incident angle dependence of the absorption spectrum as described above. The detector 14 detects the intensity of the infrared light. On the optical stage 16, the detector 14 is placed. The optical stage 16 is driven by a motor (not shown) to be moved to a position where the detected signal from the detector 14 becomes the largest, i.e., to the position where the infrared light can be detected the best, whereby the detector 14 is positioned. The position providing the best condition of the detection of the infrared light moves according to the angular change of the sample 12 caused by driving the turntable 10. This is because the optical axis from the sample 12 to the detector 14 is deviated due to a refraction of the light in the sample 12. Accordingly, the detection of the infrared light on the detector 14 can optimally be performed by providing the optical stage 16.

The unit 18 controls the operation of the infrared absorption spectrometer 100 for evaluating the piezoelectric field based on the measured result with the use of the detector 14. The detailed operation of the infrared absorption spectrometer 100 based on the control of the unit 18 will be described later.

Although the light source 2, the diffraction grating monochromator 6, the sample 12 and the detector 14 are arranged in this order in FIG. 1, the arrangement order is not limited thereto.

FIG. 2 shows a configuration of an infrared absorption spectrometer 200 according to another example using the diffraction grating monochromator 6. The infrared absorption spectrometer 200 also has the light source 2, a lens 4, a diffraction grating monochromator 6, another lens 8, a turntable 10, a detector 14, an optical stage 16 and a unit 18. In the infrared absorption spectrometer 200, each component is arranged in the order of the light source 2, the sample 12, the diffraction grating monochromator 6 and the detector 14. The function and operation of each component is the same as those in the above-mentioned infrared absorption spectrometer 100 (FIG. 1), so that the explanation thereof is omitted.

FIG. 3 shows a configuration of an infrared absorption spectrometer 300 utilizing a Fourier transform spectrometer instead of the diffraction grating spectrometer 6. The evaluation of the piezoelectric field described later is also applicable in case where the infrared absorption spectrometer 300 is used. In the infrared absorption spectrometer 300, the infrared light from the light source 2 is focused by a concave mirror 34-1, and then, guided to a beam splitter 36-1. The beam splitter 36-1 reflects a half of the incident light to direct the same to a movable mirror 36-2, while transmits the remaining half to a fixed mirror 36-3. Each light is reflected by the movable mirror 36-2 or the fixed mirror 36-3, and then, combined on the beam splitter 36-1. The combined light is focused onto the AlGaN/GaN HEMT sample 12 by a concave mirror 34-2 through a plane mirror 36-4. The detector 14 detects the light transmitted through the sample 12 to thereby be focused by the concave mirror 34-3. When the movable mirror 36-2 is scanned in a fixed direction, the optical path difference is caused in a distance between the beam splitter 36-1 and the movable mirror 36-2 and a distance between the beam splitter 36-1 and the fixed mirror 36-3. The combined waves cause interference phenomena, which is recorded as an oscillatory profile known as an interference pattern. This pattern is subjected to Fourier transform. As a result, an infrared spectrum, which exhibits absorption bands at a predetermined wavelength, is obtained. As apparent from FIGS. 2 and 3, the infrared light focusing system to the sample 12 may be either one of lens and concave mirror.

Explained hereinafter is a non-destructive evaluation method of the piezoelectric field using the infrared absorption spectroscopy according to the present invention utilizing the infrared absorption spectrometers 100 (FIG. 1), 200 (FIG. 2) or 300 (FIG. 3). Since the processing is common to any one of these spectrometers, the method is explained using the infrared absorption spectrometer 100 (FIG. 1).

Figure 4:
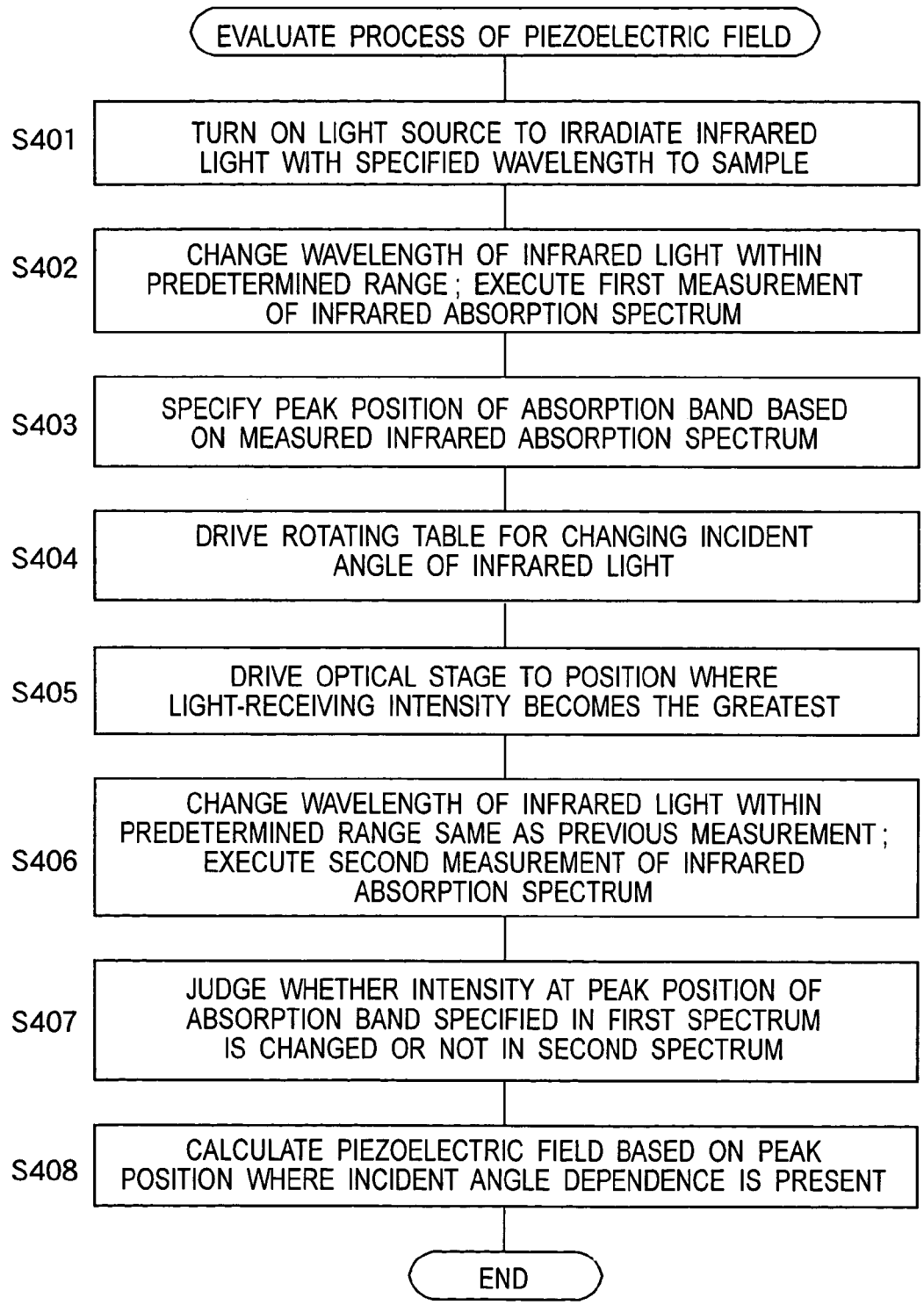
FIG. 4 is a flowchart showing procedures for evaluating a piezoelectric field.

FIG. 4 shows a flow of an evaluation process of the piezoelectric field. The following process is performed mainly based on the control by the unit 18. It is supposed that a spectrum $I_1$ which is a reference for judging whether infrared light is absorbed or not, is measured before the following process. The spectrum $I_1$ is measured in the state that the sample 12 does not exist. At first, the light source 2 of the infrared absorption spectrometer 100 (FIG. 1) is turned on. Thus, to the sample 12, infrared light with a specified wavelength resolved by the diffraction grating monochromator 6 (S401) illuminates. In this case, it is unnecessary to destroy or process the sample 12. The wavelength of the infrared light is changed within a predetermined range, thereby executing the first measurement of the infrared absorption spectrum by the detector 14 (S402). As described above, the wavelength range to be measured is set to approximately several Am to several ten $\mu$m, considering that the expected piezoelectric field strength is 0.1 to 1.0 MV/cm. Assuming that the wavelength is changed within the range of 1 $\mu$m to 2 $\mu$m, for example. The infrared absorption spectrum $I_2$ is obtained by subtracting the observed spectrum as the irradiation result of the infrared light from the reference spectrum. The energy of the absorbed wavelength has a great difference, so that the peak position can be specified. It is needless to say that the absorption of the infrared light cannot occur in the area where the two-dimensional electron gas is not present. The unit 18 of the infrared absorption spectrometer 100 specifies the peak position of the absorption band based on the measured infrared absorption spectrum $\log(I_1/I_2)$ (S403)

Referring again to FIG. 1, the infrared absorption spectrometer 100 subsequently drives the turntable 10 with an optional angle for changing the incident angle of the infrared light to the sample 12 (S404). When the target incident angle is obtained, a setting complete signal is sent from the turntable 10 to the unit 18 via the signal line. When receiving the setting complete signal of the incident angle, the unit 18 moves the optical stage 16 by a constant distance to drive the optical stage 16 to a position where the intensity of the detected light becomes the strongest (S405). This allows to specify the wavelength of the infrared light that is strongly absorbed. When the optical stage 16 is positioned, the optical stage 16 sends a moving complete signal to the unit 18. Alternately, a signal from the detector 14, which is obtained by repeating a series of measurement by several times, may be plotted as a function of the position of the optical stage 16, thereby being capable of determining the position of the optical stage 16 where the signal from the detector 14 becomes the largest. Further, in case where the concave mirror 34-3 (FIG. 3) is used for the focusing system like the infrared absorption spectrometer 300 (FIG. 3), a mechanism for adjusting the angle of the concave mirror 34-3 is also required.

Thereafter, the unit 18 changes the wavelength of the infrared light within the range same as that in the previous measurement for performing the second measurement of the infrared absorption spectrum (S406). The unit 18 judges whether the intensity at the peak position of the absorption band specified in the first spectrum is changed or not in the second spectrum (S407). The case where the intensity of the absorption band changes means that there is incident angle dependence. The unit 18 calculates the piezoelectric field based on the peak position where the incident angle dependence is present (S408).

Figure 5:
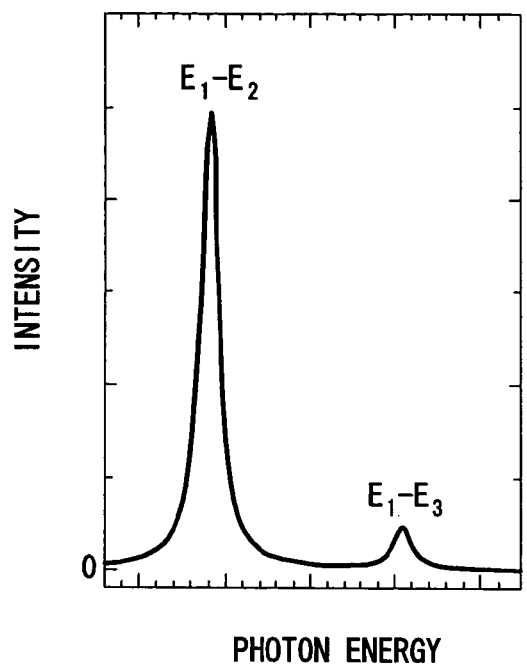
FIG. 5 is a view showing an absorption spectrum of a given sample.
Figure 6:
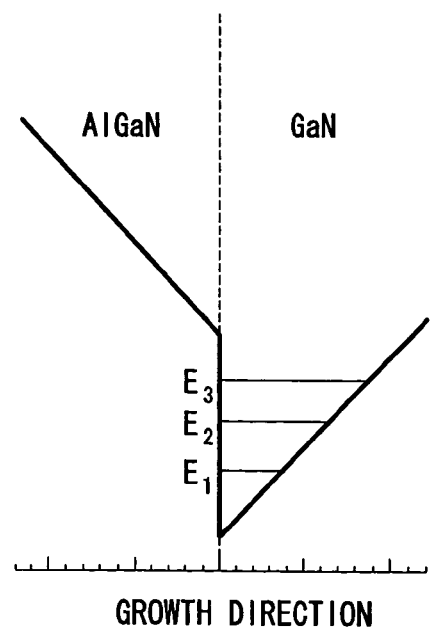
FIG. 6 is a view showing a potential structure and energy levels of a two-dimensional electron gas formed at an AlGaN/GaN interface.

FIG. 5 shows a spectral distribution of the measured infrared light. In FIG. 5, peaks are positioned at the photon energy of ($E_1$–$E_2$) and ($E_1$–$E_3$). It is supposed that the absorption bands have the dependence of the intensity on the incident angle. FIG. 6 shows a potential structure and a level of two-dimensional electron at the AlGaN/GaN interface. The peak position of the absorption band reflects the energy level of the two-dimensional electron determined by the potential structure of AlGaN/GaN shown in FIG. 6. The electron energy level with the n-th (n=1, 2, 3, . . . ) quantum state is represented by the equation of electron energy level (equation 1) showing the relationship between the piezoelectric field and the electron energy level.

$$E_n = \left(\frac{1}{2m^*}(h/2\pi)^2\right)^{1/3}\left[\frac{3\pi eF}{2}\left(n-\frac{1}{4}\right)\right]^{2/3} \quad \text{[Equation 1]}$$

In the equation 1, h/2$\pi$ represents the Plank constant, e representing an elementary electric charge, m* representing an effective electron mass, and F representing a piezoelectric field. Since almost all electrons are in a state of n=1 at the room temperature or below, the observed peak position (h/2$\pi$)$\omega$ of the absorption band is obtained as follows.

$$(h/2\pi)\omega = E_j - E_1 (j=1,2,3,\dots) \quad \text{[Equation 2]}$$

The piezoelectric field strength F can be obtained by using the equation 1 and the equation 2. Specifically, the piezoelectric field can be quantitatively evaluated according to the above-mentioned procedure.

[Second Embodiment]

The second embodiment explains an infrared absorption spectrometer according to another example that can measure an infrared absorption spectrum of two-dimensional electron gas in an AlGaN/GaN HEMT sample. In such infrared absorption spectrometer, an automatic correction mechanism (the optical stage 16 in FIG. 1) with respect to the deviation of the optical axis is unnecessary.

Figure 7:
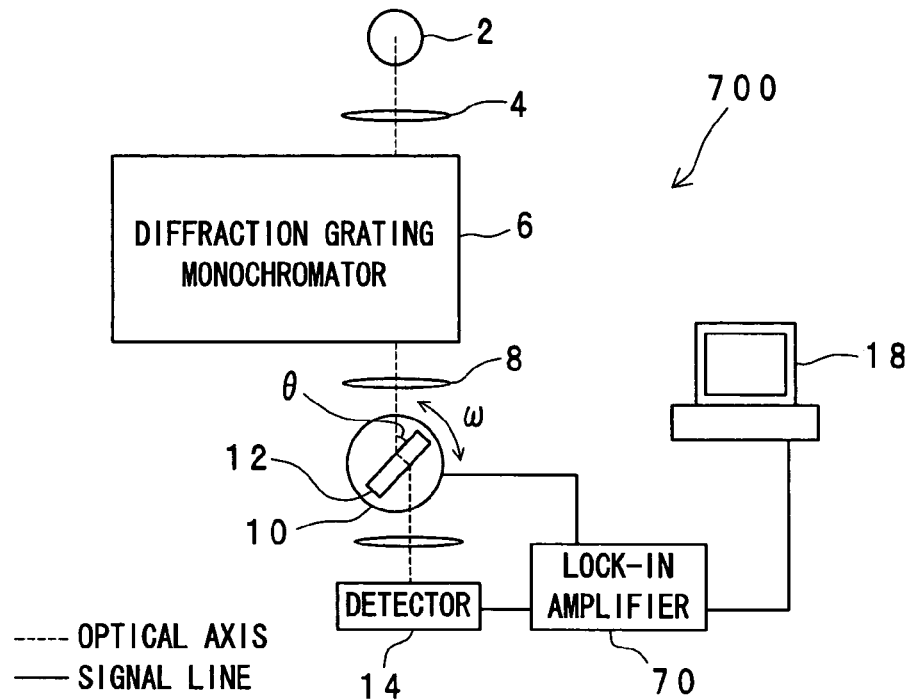
FIG. 7 is a view showing a configuration of an infrared absorption spectrometer equipped with a sample rotating mechanism which enables the use of a lock-in detection method.

FIG. 7 shows an infrared absorption spectrometer 700 equipped with a sample rotating mechanism. Because the sample rotating mechanism enables the modulation of the incident angle, a lock-in detection technique is applied to the spectrometer 700. The infrared absorption spectrometer 700 is different from the infrared absorption spectrometer 100 (FIG. 1) in the configuration of the turntable 10, in which a lock-in amplifier 70 is provided and the optical stage 16 (FIG. 1) is not present in the infrared absorption spectrometer 700. The different points are explained hereinafter. The other configurations and operations are the same as those of the infrared absorption spectrometer 100, so that the explanation thereof is omitted.

The turntable 10 can slightly rotate with an angular frequency ω about a certain angle θ. The angular amplitude of the small rotation is set to a degree that the optical axis is not deviated from the light-receiving surface of the detector 14. The sample to be measured is slightly rotated, and then, is illuminated by the infrared light to detect a signal having a frequency same as the frequency ω of the small rotation, whereby only the information sent from the sample 12 is obtained. Specifically, an AC signal of the angular frequency ω obtained by this measurement system includes only a signal caused by the absorption band having incident angle dependence. The lock-in amplifier 70 detects only the AC component with the angular frequency ω among the signals obtained by the detector 14. The absorption band of the two-dimensional electron system having the incident angle dependence can sensitively be detected by the lock-in amplifier 70. When the measured value of the absorption band detected by the lock-in amplifier 70 is transmitted to the unit 18, the unit 18 specifies the absorption band based on the value, thereby being capable of quantitatively evaluating the piezoelectric field according to the procedure explained in the first embodiment. A well-known lock-in voltmeter can be used instead of the lock-in amplifier.

Figure 8:
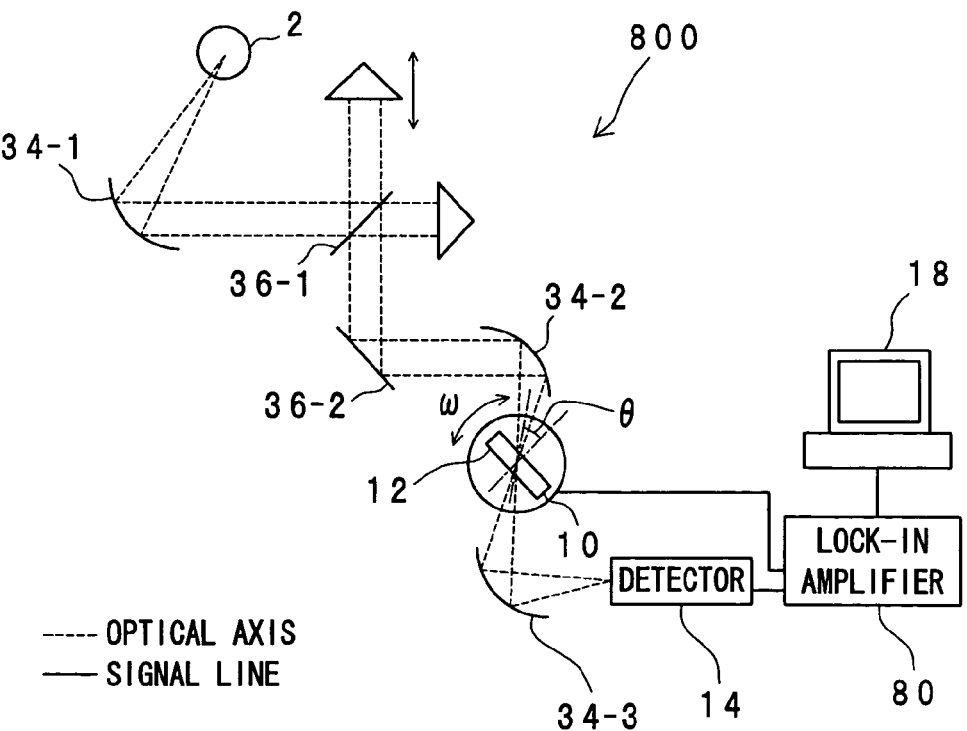
FIG. 8 is a view showing a configuration of an infrared absorption spectrometer performing lock-in detection by utilizing a Fourier transform spectrometer.

FIG. 8 shows a configuration of an infrared absorption spectrometer 800 performing the lock-in detection by utilizing a Fourier transform spectrometer. The infrared absorption spectrometer 800 corresponds to the infrared absorption spectrometer 500 (FIG. 5), and differs from the same in the configuration of the turntable 10, in which a lock-in amplifier 80 is provided and the optical stage 16 (FIG. 3) is not present in the infrared absorption spectrometer 800. These points are the same as the infrared absorption spectrometer 700 (FIG. 7), so that the explanation thereof is omitted.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. A method of evaluating a piezoelectric field comprising:

measuring a first absorption spectrum of a sample by irradiating the sample with infrared light at a first angle;

measuring a second absorption spectrum of the sample by irradiating the sample with the infrared light at a second angle, different from the first angle;

specifying a peak position of an absorption band having incident-angle dependent intensity based on the first absorption spectrum and the second absorption spectrum; and obtaining the piezoelectric field strength using a relationship between the piezoelectric field and electron energy level corresponding to the peak position of the absorption band.

2. The method according to claim 1, wherein the piezoelectric field is an electric field induced by a lattice-mismatch strain in a semiconductor heterojunction of the sample.

3. The method according to claim 1, wherein measuring the first absorption spectrum includes:

measuring, in advance, a reference spectrum by changing wavelength of the infrared light within a predetermined range;

irradiating the sample with the infrared light and changing the wavelength of the infrared light within the predetermined range; and calculating the first absorption spectrum based on the infrared light which is transmitted through the sample.

4. The method according to claim 1, wherein measuring the second absorption spectrum includes irradiating the sample with the infrared light at the second angle by rotating a turntable on which the sample is placed.

5. The method according to claim 4, wherein measuring the second absorption spectrum includes:

detecting deviation of an optical axis of the infrared light which irradiates the sample and is transmitted through the sample;

correcting the deviation of the optical axis; and calculating the second absorption spectrum based on the infrared light which is transmitted through the sample.

6. A method of evaluating a piezoelectric field comprising:

measuring a first absorption spectrum of a sample by irradiating the sample with infrared light;

measuring a second absorption spectrum of the sample by irradiating the sample, while placed on a turntable, with infrared light, and vibrating the turntable with a predetermined angular frequency;

specifying a peak position of an absorption band having incident-angle dependent intensity based on the first absorption spectrum and the second absorption spectrum; and obtaining the piezoelectric field strength using a relationship between the piezoelectric field and electron energy level corresponding to the peak position.

* * * * *